United States Patent [19]
Byas-Smith

[11] Patent Number: 5,762,963
[45] Date of Patent: Jun. 9, 1998

[54] METHOD AND COMPOSITIONS FOR CONTROLLING ORAL AND PHARYNGEAL PAIN USING CAPSAICINOIDS

[75] Inventor: Michael G. Byas-Smith, Decatur, Ga.

[73] Assignee: Emory University, Atlanta, Ga.

[21] Appl. No.: 478,554

[22] Filed: Jun. 7, 1995

[51] Int. Cl.$^6$ .......................... A61K 9/24; A61K 31/16; A01N 37/18

[52] U.S. Cl. .................. 424/472; 424/440; 424/441; 424/464; 424/482; 514/627; 514/563; 514/487; 514/557

[58] Field of Search .................. 424/440, 441, 424/464, 472, 484; 514/627, 563, 487, 557

[56] References Cited

U.S. PATENT DOCUMENTS

| | | | |
|---|---|---|---|
| 3,903,297 | 9/1975 | Robert | 424/305 |
| 4,289,795 | 9/1981 | Bogentoft et al. | 427/3 |
| 4,313,958 | 2/1982 | LaHann | 424/324 |
| 4,401,663 | 8/1983 | Buckwalter et al. | 424/321 |
| 4,424,205 | 1/1984 | LaHann et al. | 424/72 |
| 4,424,206 | 1/1984 | Ohmura et al. | 424/101 |
| 4,443,473 | 4/1984 | Buckwalter et al. | 424/300 |
| 4,460,602 | 7/1984 | Buckwalter et al. | 424/322 |
| 4,493,848 | 1/1985 | LaHann et al. | 424/324 |
| 4,532,139 | 7/1985 | Janusz et al. | 514/627 |
| 4,544,668 | 10/1985 | Janusz et al. | 514/563 |
| 4,544,669 | 10/1985 | LaHann et al. | 514/563 |
| 4,564,633 | 1/1986 | LaHann et al. | 514/538 |
| 5,035,882 | 7/1991 | Hussein et al. | 424/58 |
| 5,126,147 | 6/1992 | Silvestri et al. | 424/497 |
| 5,273,754 | 12/1993 | Mann | 424/440 |

FOREIGN PATENT DOCUMENTS

| | | | |
|---|---|---|---|
| 0 068 590 | 1/1983 | European Pat. Off. | C07C 127/17 |
| 0 068 591 | 1/1983 | European Pat. Off. | C07C 143/75 |
| 0 068 592 | 1/1983 | European Pat. Off. | C07C 125/065 |
| 0 089 710 | 9/1983 | European Pat. Off. | C07C 103/76 |
| 0 149 545 | 7/1986 | European Pat. Off. | A61K 31/615 |
| 3-251522 | 11/1991 | Japan | A61K 7/16 |

OTHER PUBLICATIONS

Ansel, et al., (Editors), *Pharmaceutical Dosage Forms and Drug Delivery Systems*, 6th Edition (Williams & Wilkins, Malvern, New Jersey, 1995), Chapter 3, pp. 78–80.

Ansel, et al., (Editors), *Pharmaceutical Dosage Forms and Drug Delivery Systems*, 6th Edition (Williams & Wilkins, Malvern, New Jersey, 1995), Chapter 5, pp. 164–223.

Bennett, et al., "Constitution and Biosynthesis of Capsaicin," *J. Chem. Soc. (C)*, pp. 442–446 (1968).

Berger, et al., "Capsaicin Candy as a Possible Treatment of Oral Pain in Patients Receiving Cancer Therapy," Thirtieth Annual Meeting of the American Society of Clinical Oncology, Dallas, Texas, May 14–17, 1994, Abstract No. 1470, vol. 13 (Mar. 1994).

Berger, et al., "Oral Capsaicin Provides Temporary Relief for Oral Mucositis Pain Secondary to Chemotherapy/Radiation Therapy," *J. Pain and Symp. Management* (In Press).

Berger, et al., "The Use of Capsaicin as a Means to Control Oral Pain," *Supportive Care in Cancer Proceedings*, (1994)*.

Bernstein, "Capsaicin and Substance P," *Clinics in Dermatology*, 9(4):497–503 (1991).

Bernstein, et al., "Topical capsaicin treatment of chronic postherpetic neuralgia," *J. of Am. Acad. Dermatol.*, 21(2):265–270 (1989).

Bernstein, et al., "Treatment of chronic postherpetic neuralgia with topical capsaicin," *J. of Am. Acad. of Dermatol.*, 17(1):93–96 (1987).

Brand, et al., "Anti-inflammatory pharmacology and mechanism of the orally active capsaicin analogs, NE-19550 and NE-28345," *Agents and Action*, 31(3–4):329–340 (1990).

Brand, et al., "NE-19550: A Novel, Orally Active Anti-Inflammatory Analgesic," *Drugs. Exptl. Clin. Res.*, XIII(5):259–265 (1987).

Buck and Burks, "The Neuropharmacology of Capsaicin: Review of Some Recent Observations," *Pharm. Reviews*, 38(3):179–226 (1986).

Byas–Smith, et al., "A Study of the Thermal Sensory Effects of Hot Pepper on the Oral Mucosa in Humans," Study #255–94*.

Carpenter, et al., "Vascular and Sensory Responses of Human Skin to Mild Injury After Topical Treatment with Capsaisin," *Bri. J. of Pharmacol.*, 73:755 (1981).

Cline, et al., "Standardization of the Visual Analogue Scale," *Nursing Research*, 41(6):378–380 (1992).

Cordell, et al., "Capsaicin: Identification, Nomenclature, and Pharmacotherapy," *The Annals of Pharmacotherapy*, 27(3):330–336 (1993).

(List continued on next page.)

*Primary Examiner*—Chhaya D. Sayala
*Attorney, Agent, or Firm*—Sherry M. Knowles; King & Spalding

[57] ABSTRACT

Methods and compositions are provided for the oral delivery of temporally increasing concentrations of capsaicin, its derivatives, and analogs (collectively, "capsaicinoids"), to provide oral or pharyngeal analgesia while minimizing sensations of nausea and burning associated with the oral administration of capsaicinoids. The methods and compositions described herein soothe and relieve oral or pharynx pain. In one embodiment, one or more capsaicinoids are dispersed within a lollipop, with successively decreasing concentrations of capsaicin from the center out to the periphery, and administered to a patient in need of amelioration of oral pain. Alternatively, the capsaicinoid can be dispersed, with decreasing concentrations from the center to the periphery, in a tablet, caplet, lozenge, troche, pill, candy, or similar formulation. Capsaicinoids include dihydrocapsaicin, norhydrocapsaicin, homocapsaicin, homodihydrocapsaicin I, norhydrocapsaicin, homodihydrocapsaicin, nordihydrocapsaicin, civamide, nonivamide, NE-19550 (also called olvanil), NE-21610, NE-28345 (also called N-oleyl-homovanillamide), their analogs, and derivatives.

45 Claims, 1 Drawing Sheet

OTHER PUBLICATIONS

Cordell, et al., *Webster's Ninth New Collegiate Dictionary*, pp. 331, 871 (Editor, F. C. Mish, et al., Merriam Webster, Inc., Springfield, MA 1991)*.

Crombie, et al., "Amides of Vegetable Origin. Part VI. Synthesis of Capsaicin," *Journal of the Chemical Society*, pp. 1025–1027 (1955).

Dray, et al., "NE–19550 and NE–21610, antinociceptive capsaicin analogues; studies on nociceptive fibres of the neonatal rat tail in vitro," *Eur. J. Pharmacol.*, 181(3):289–293 (1990).

Epstein, et al., "Topical application of capsaicin for treatment of oral neuropathic pain and trigeminal neuralgia," *Oral Surgery Oral Medicine Oral Pathology*, 77(2):135–140 (1994).

Fitzgerald, et al., "Capsaicin and Sensory Neurones—A Review," *Pain*, 15:109–130 (Elsevier Biomedical Press, 1983).

Gamse, "Capsaicin and Nociception in the Rat and Mouse," *Naunyn–Schmiedeberg's Arch. Pharmacol.*, 320:205–216 (1982).

Gazelius, et al., "Reduction of substance P (SP) levels in cat dental pulp by capsaicin," *J. of Dental Res.*, 62(1):139 (1983).

Green, "Sensory interactions between capsaicin and temperature in the oral cavity," *Chem. Senses*, 11(3):371–382 (1986).

Holzer, et al., "Distribution of Capsaicin–Sensitive Nerve Fibres Containing Immunoreactive Substance P in Cutaneous and Visceral Tissues of the Rat," *Neuroscience Letters*, 31:253–257 (1982).

Jancso, "Desensitization with Capsaicin and Related Acylamides as a Tool for Studying the Function of Pain Receptors," *Proceedings of the 3rd Intl. Pharmacological Meeting, Pharmacology of Pain* (Editor, R. K.S. Lim, 9:33–55, Pergamon Press, Oxford, England 1968).

Jancso, et al., "Pharmacologically induced selective degeneration of chemosensitive primary sensory neurones," *Nature*, 270(22/29):741–743 (1977).

Jessell, et al., "Capsaicin–induced depletion of substance P from primary sensory neurones," *Brain Res.*, 152:183–188 (1978).

Lundberg, et al., "Capsaicin–induced desensitization of airway mucosa to cigarette smoke, mechanical and chemical irritants," *Nature*, 302:251–253 (1983).

Magge, et al., "The Sensory–Efferent Function of Capsaicin–Sensitive Sensory Neurones," *Gen. Pharmacol.*, 19(1):1 (1988).

Maggi, "Therapeutic Potential of Capsaicin–like Molecules––Therapeutic Potential of Capsaicin–Like Molecules: Studies in Animals and Humans," *Life Sciences*, 51:1777–1781 (Pergamon Press, 1992).

Marshall, "Solid Oral Dosage Forms," *Modern Pharmaceutics*, 7:359–427 (Editors, Yalkowsky and Swarbrick, Marcel Dekker, Inc., New York and Basel, 1979).

McCormack, et al., "Clinical applications of visual analogue scales: a critical review," *Psychological Medicine*, 18:1007–1019 (1988).

Micko, "Zur Kenntniss des Capsaicins," *Zeitschrift fur Untersuchung der Nahrungs– und Genussmittel*, 818–829 (1898).

Molnar, et al., "Effect of Capsaicin on the Isolated Ileum and Auricle of the Guinea Pig," *Acta Physiologica Academiae Scientiarum Hungaricae*, 35(3–4):369–374 (1969).

Molnar, "Die pharmakologischen Wirkungen des Capsaicins, des scharf schmeckenden Wirkstoffes im Paprika," *Arzneimittel–Forschung*, 718–727 (1965).

Monsereenusorn, et al., "Capsaicin—A Literature Survey," *Critical Reviews in Toxicology*, 10(4):321–339 (CRC Press, Oct. 1982).

Mottola, "Measurement Strategies: The Visual Analogue Scale," *Decubitus*, 6(5):56–58 (1993).

O'Neill, "Mechanism of capsaicin action: recent learnings," *Respiratory Medicine*, 85(Supplement A):35–41 (1991).

Paus, et al., "Hair Growth Induction by Substance P," *Laboratory Investigation*, 71(1):134–140 (1994).

Ray, et al., "Morphine, but not sodium cromoglycate, modulates the release of substance P from capsaicin–sensitive neurones in the rat trachea in vitro," *Br. J. Pharmacol.*, 102:797–800 (1991).

Rozin, "The Use of Characteristic Flavorings in Human Culinary Practice," *Flavor: Its Chemical, Behavioral, and Commercial Aspects*, Chapter 9, pp. 101–127 (C.M. Apt, Editor, Westview Press, Boulder, CO, 1978).

Rozin, et al., "The role of desensitization to capsaicin in chili pepper ingestion and preference," *Chemical Senses*, 6(1):23–31 (1981).

Rumsfield, et al., "Topical Capsaicin in Dermatologic and Peripheral Pain Disorders," *DICP, The Annals of Pharmacotherapy*, 25:381–387 (1991).

Schachtel, et al., "Ratings scales for analgesics in sore throat," *Clin. Pharmacol. Ther.*, 36:151–156 (1984).

Schachtel, "Sore Throat Pain," *Advances in Pain Research and Therapy: The Design of Analgesic Clinical Trials*, 18:393–407 (Editor, Max, et al., Raven Press, Ltd., New York, 1991).

Schachtel, et al., "Subjective and objective features of sore throat," *Arch. Intern. Med.*, 144:497–500 (1984).

Schachtel, et al., "Sore throat pain in the evaluation of mild analgesics," *Clin. Pharmacol. Ther.*, 44:707–711 (1988).

Schachtel, et al., "Caffeine as an analgesic adjuvant: a double–blind study comparing aspirin with caffeine to aspirin and placebo in patients with sore throat," *Arch. Intern. Med.*, 151:733–737 (1991).

Simon, "Optimal two–stage designs for phase II clinical trials," *Controlled Clinical Trials*, 10:1–10 (1989).

Simon, "How Large Should a Phase II Trial of a New Drug Be?" *Cancer Treatment Reports*, 71(11):1079–1085 (1987).

Stevens and Lawless, "Enhancement of Responses to Sequential Presentation of Oral Chemical Irritants," *Physiol. & Behav.*, 39:63–65 (1987).

Tandan, et al., "Topical Capsaicin in Painful Diabetic Neuropathy," *Diabetes Care*, 15(1):8–14 (1992).

Thall and Simon, "Practical Bayesian Guidelines for Phase IIB Clinical Trials," *Biometrics*, 50:337–349 (1994).

Thresh, "Capsaicin, the Active Principle of Capsicum Fruits," *The Pharmaceutical Journal and Transaction*, p. 21 (Jul. 8, 1876).

Vig, et al., "A New Synthesis of N–(4'–Hydroxy–3'–methoxybenzyl)–8–methyl–non–6(E)–enamide (Capsaicin)," *Indian Journal of Chemistry*, 17B:558–559 (1979).

Virus, et al., "Pharmacologic Actions of Capsaicin: Apparent Involvment of Substance P and Serotinin," *Life Sciences*, 25:1273–1284 (1979).

Walker, "Capsaicin: Properties, reactions and uses," *Manufacturing Chemist and Aerosol News*, 42:35–36 (1968).

Wallengren and Moller, "The Effect of Capsaicin on Some Experimental Inflammations on Human Skin," *Acta Derm. Venereol. (Stockh)*, 66:375–380 (1986).

Yaksh, et al., "Intrathecal Capsaicin Depletes Substance P in the Rat Spinal Cord and Produces Prolonged Thermal Analgesia," *Science*, 206:481–483 (1979).

Zaidi, et al., "Experimental peptic ulceration: I. The significance of mucous barrier," *Indian J. Med. Res.* 46(27):732 (1958).

Zaidi, et al., "IV. Effect of mucous stimulant on histamine induced ulceration," *Indian J. Med. Res.*, (1958).

*Manufacturing Confectioner* (monthly publication) (Manufacturer Confectioner Publishing Co., Glen Rock, NJ 07452 (1956 to present).

*Confectionery Production* (monthly publication) (Specialized Publications, Ltd., Surbiton, Surrey KT6 4BT England).

*The New Encyclopaedia Britannica*, 15th Edition, 19:394–397, 406 (Chicago, 1992).

*The Encyclopedia Americana*, 5:538–539 (Grolier, Inc., Danbury, Connecticut, 1992).

*The New Encyclopaedia Brittanica*, 15th Edition, 21:321–322, 383 (Chicago, 1992).

*The New Encyclopaedia Britannica*, 15th Edition, 23:821–822, 828 (Chicago, 1992).

*Physician's Desk Reference*, 15th Edition, p. 426 (1994).

"Treatment of Painful Diabetic Neuropathy with Topical Capsaicin," *Arch. Intern. Med.*, 151:2225–2229 (1991).

*The Merck Index*, 11$^{th}$ Edition, p. 266, Entry #1767 (Editor, S. Budavari, et al., Merck & Co., Inc., Rahway, NJ 1989).

*The Merck Index*, p. 1398, Entry #8834 (1989).

METHOD AND COMPOSITIONS FOR CONTROLLING ORAL AND PHARYNGEAL PAIN USING CAPSAICINOIDS

BACKGROUND OF THE INVENTION

The present invention is in the field of pain relief, and more specifically is a method and composition for controlling oral and pharyngeal pain through the controlled release of capsaicin.

For thousands of years, spices have added appealing taste properties to otherwise relatively bland meats, vegetables, and cereals. Spices in the fruits of plants of the genus Capsicum have the oldest recorded and the widest use in the cuisines of the world. Perhaps as many as one quarter of the world's population ingest Capsicum on a daily basis. G. A. Cordell, et al., "Capsaicin: Identification, Nomenclature, and Pharmacotherapy," *The Annals of Pharmacotherapy*, pp. 330–336 (March 1993); P. Rozin, "The Use of Characteristic Flavorings in Human Culinary Practice," pp. 101–127 in Ch. 9 of C. M. Apt, editor, *Flavor: Its Chemical, Behavioral, and Commercial Aspects* (Westview Press, Boulder, Colo. 1978). Diego Alvarez Chauca, the physician on the second of Columbus' expeditions to the Americas, observed not only the culinary, but also the medicinal uses of Capsicum. The Genus Capsicum is a member of the family Solanaceae (which includes tomatoes, potatoes, and the deadly nightshades). Chili pepper, red pepper, paprika, and capsicum, are all species of Capsicum. Capsicum has been described as the dried, ripe fruit of *C. frutescens* L., *C. annum* L. var. *conoides* Irish, or *C. annum* var. *longum* Sendt. Cordell, et al., at p. 331;p. 871 of *Webster's Ninth New Collegiate Dictionary*, ed. by F. C. Mish, et al. (Merriam Webster, Inc. Springfield, Mass. 1991).

The most recognized property of capsicum and chilies is their pungency. The most potent and predominant chemical entity found in the fruit of the plant, and responsible for the sensory effects associated with pungency, is the parent compound capsaicin ((E)-N-[(4-hydroxy-3-methyoxyphenyl)methyl]-8-methyl-6-nonenamide); see p. 266, entry no. 1767 in The Merck Index, 11th Edition, ed. by S. Budavari, et al. (Merck & Co., Inc. Rahway, N.J. 1989); Sigma Chemical Co., St. Louis, Mo. 63178. Capsicum fruits contain about 0.1 to 1.0% capsaicin. Y. Monsereenusorn, et al., "Capsaicin—A Literature Survey," *Critical Reviews in Toxicology*, vol. 10, issue 4, 321–339 (CRC Press October 1982). Capsaicin has the following structure.

A series of homologous branched- and straight-chain alkyl vanillylamides, known as capsaicinoids, also occur in the fruit of the capsicum plants at concentrations less than the parent compound, ranging from approximately 0.1 to 1.0 percent.

Cordell, et al., at p. 330; D. J. Bennett, et al., "Constitution and Biosynthesis of Capsaicin," *J. Chem. Soc. (C)*, pp. 442–446 (1968). Examples of some of these compounds are set out below.

[dihydrocapsaicin; 8-methyl-octanoic acid vanillylamide]

[Norhydrocapsaicin; 7-methyl-octanoic acid vanillylamide]

[homocapsaicin; 9-methyldec-trans-7-enoic acid vanillylamide]

[homodihydrocapsaicin; 9-methyldec-trans-7-enoic acid vanillylamide]

(MW = 321) 9-methyl-decanonic acid vanillylamide

[homodihydrocapsaicin I]

Civamide is the non-naturally occurring cis isomer of capsaicin, and has the chemical name N-[(4-hydroxy-3-methoxyphenyl)-methyl]-8-methyl-(Z)-6-nonemamide.

Nonivamide (N-[(4-hydroxy-3-methoxyphenyl)methyl]-nonamide), also erroneously referred to as "synthetic capsaicin," has the following structure.

NE-19550 (also called olvanil, N-[4-hydroxy-3-methoxyphenyl) methyl]-9Z-octadecenamide))

NE-28345 (also called N-oleyl-homovanillamide, formally named N-(9Z-octadecenyl)-3-methoxy-4-hydroxyphenylacetamide)

Capsaicinoids are also described in E.P.A. No. 0 149 545 filed by the Procter & Gamble Co., and published on 24 Jul. 1986, incorporated herein by reference.

For centuries, people have known that capsicum seeds contain a substance that produces intense erythema, pain, and inflammation when applied to skin or mucous membranes. J. E. Bernstein, "Capsaicin and Substance P," *Clinics in Dermatology*, vol. 9, no. 4, pp. 497–503 (October–December 1991). However, chronic capsaicin treatment, either topically or parenterally, produces an insensitivity to almost all types of chemical irritation which persists for several months while responses to light touch and mechanical stimulation are unimpaired. R. M. Virus, et al., "Pharmacologic Actions of Capsaicin: Apparent Involvement of Substance P and Serotonin," *Life Sciences*, vol. 25, pp. 1273–1284 (1979); see also J. M. Lundberg, et al., "Capsaicin-induced desensitization of airway mucosa to cigarette smoke, mechanical and chemical irritants," *Nature*, vol. 302, pp. 251–253 (March 17, 1983). The recovery from this general desensitization to all potent substances is uniformly slow and may not be complete even after 60 days. Y. Monsereenusorn, et al., at p. 329; p. 115 of M. Fitzgerald, "Capsaicin and Sensory Neurones–A Review," *Pain*, vol. 15, pp. 109–130 (Elsevier Biomedical Press 1983); N. Jansc ó, "Desensitization with Capsaicin and Related Acylamides as a Tool for Studying the Function of Pain Receptors," *Proceedings of the 3rd Intl. Pharmacological Meeting*, 1966, *Pharmacology of Pain*, ed. by R. K. S. Lim, vol. 9, pp. 33–55 (Pergamon Press Oxford, Eng. 1968).

The ability of capsaicin to induce desensitization to chemical substances generally has been attributed to its ability to deplete substance P from local sensory terminals. Substance P, an undecapeptide widely distributed in afferent sensory fibers, functions as a neurotransmitter for the communication of pain and some itch sensations from the periphery to the central nervous system. It is found primarily in type-C fibers and some type-A delta fibers. Substance P is also an important mediator of inflammation in a variety of tissues, including the skin. Bernstein, at p. 497; Cordell, et al., at p. 334; see entry no. 8834, p. 1398 of *The Merck Index* (1989). Noxious stimuli prompt release of substance P from sensory neurons distally toward the skin and joints and centrally into the spinal cord and brain stem. Release of substance P into distal tissues triggers a cascade of events associated with neurogenic inflammation. When a sensory neuron is exposed to purified capsaicin, the neuron releases; its supply of substance P, and upon repeated application, stops producing substance P. The neuron's ability to send a pain signal is diminished without substance P. After topical application of capsaicin is discontinued, substance P stores revert to pretreatment levels, and neuronal sensitivity returns to normal. Cordell, et al.,at p. 334.

Capsaicin has not been shown to be ulcerogenic even though spicy foods are commonly reported to exacerbate symptoms in patients with gastrointestinal disease. (Zaidi, S. H., et al., "Experimental peptic ulceration. I. The significance of mucous barrier"; Zaidi, S. H., et al., "IV. Effect of mucous stimulant on histamine induced ulceration," *Indian J. Med. Res.*, 1958:46;27;732). Capsaicin does increase the speed of gastric emptying and this may explain some of the gastrointestinal upset.

The dosage forms of capsaicin that have been most widely studied clinically are homogeneous capsaicin-containing creams for topical applications (Zostrix, Zostrix-hP, and Axsain (Zostrix GenDerm Corp., Northbrook, Ill.). These products have been shown to be effective in managing painful conditions such as rheumatoid arthritis, osteoarthritis, diabetic neuropathy, postherpetic neuralgia, postmastectomy pain syndrome, cluster headache, and reflex sympathetic dystrophy. Cordell, et al., at p. 334; J. A. Rumsfield, et al., "Topical Capsaicin in Dermatologic and Peripheral Pain Disorders," *DICP, The Annals of Pharmacotherapy*, vol. 25, pp. 381–387 (April 1991).

Capsicum has also been administered in a homogeneous oral formulation, "Throat Discs®", manufactured for Marion Merrell Dow Inc., Cincinnati, Ohio 45215, and sold over the counter. "Throat Discs®" are manufactured by SmithKline Beecham (pp. 426, 720 of *Physicians Desk Reference for Nonprescription Drugs*, 15th edition, medical consultant R. Arky (Medical Economics Data Production Co. Montvale, N.J. 07645). However, the amount of capsaicin in the product is minimal, main ingredient is not capsaicin. Furthermore, the discs do not release capsaicin in a graded fashion.

Capsicum has also been formulated as a homogeneous candy for treatment of oral pain in patients receiving cancer therapy. Ann Berger, et al., "Capsaicin Candy as a Possible Treatment of Oral Pain in Patients Receiving Cancer Therapy," *ASCO Proceedings* (May 1994); Ann Berger, et al., "The Use of Capsaicin as a Means to Control Oral Pain," *Supportive Care in Cancer Proceedings* (1994). However, these studies report some side effects such as initial burning sensations and nausea.

U.S. Pat. No. 5,035,882 to M. M. Hussein, et al., issued Jul. 30, 1991, discloses a "chloroform substitute" of capsaicin, capsicum extract, hot pepper oil, and hot pepper extract in a syrup or a candy lozenge. Each particular formulation described has a uniform concentration of the active ingredient throughout (Col. 4, line 16 of the '882 patent).

U.S. Pat. No. 4,493,848 to T. R. LaHann and B. L. Buckwalter, issued Jan. 15, 1985; U.S. Pat. No. 4,532,139 to J. M. Janusz and T. R. LaHann, issued Jul. 30, 1985; U.S. Pat. No. 4,564,633 to T. R. LaHann and B. L. Buckwalter, issued Jan. 14, 1986; U.S. Pat. No. 4,544,668 to J. M. Janusz, B. L. Buckwalter, and T. R. LaHann, issued Oct. 1, 1985; U.S. Pat. No. 4,544,669 to T. R. LaHann, J. M. Janusz, and B. L. Buckwalter, issued Oct. 1, 1985, all incorporated by reference, disclose oral delivery of solid dosage forms of N-phenylmethylalkenamide capsaicin derivatives purportedly useful for producing analgesia.

European Patent Application 0 089 710, filed by the Procter & Gamble Co., (inventors T. R. LaHann and B. L. Buckwalter), published Sep. 28, 1983, incorporated by reference, describes oral administration of hydroxyphenylacetamides with analgesic and anti-irritant activity. Similarly, analgesic and anti-irritant activity is disclosed for oral administration of N-vanillylsulfonamides in European Patent Application 0 068 591, by the Procter & Gamble Co. (inventors B. L. Buckwalter and T. R. LaHann), published Jan. 5, 1983; N-vanillylureas in European Patent Application 0 068 590, by the Procter & Gamble Co., (inventors B. L. Buckwalter and T. R. LaHann) published Jan. 5, 1983; N-vanillylcarbamates in European Patent Application 0 068 592, by the Procter & Gamble Co. (inventors B. L. Buckwalter and T. R. LaHann), published Jan. 5, 1983, all incorporated by reference.

A number of patents or patent applications disclose that side effects associated with intraperitoneal administration of capsaicin presumably can be reduced by administering increasing doses, separated preferably by a period of two hours. These patents and patent applications include European Patent Application 0 089 710, European Patent Application 0 068 591, European Patent Application 0 068 590, European Patent Application 0 068 592, U.S. Pat. No. 4,401,663, entitled, "Novel Sulfonamide Derivatives," issued Aug. 30, 1983, to B. L. Buckwalter and T. R. LaHann; U.S. Pat. No. 4,424,205 issued Jan. 3, 1984, to T. R. LaHann, entitled, "Hydroxyphenylacetamides Having Analgesic and Anti-Irritant Activity"; U.S. Pat. No. 4,443,473, entitled, "Carbamate Derivatives," issued Apr. 17, 1984, to B. L. Buckwalter and T. R. LaHann; and U.S. Pat. 4,460,602, entitled, "Urea Derivatives," issued Jul. 17, 1984, to B. L. Buckwalter and T. R. Lahann.

The effect of a parenteral injection would include searing, localized pain sensation, and at very high concentrations the drug would cause abnormalities in the cardiovascular, nervous, and pulmonary systems. Mouth burn is the primary side-effect that limits oral administration of capsaicin, and is not pertinent to parenteral administration of capsaicin.

While the above-described oral capsaicin formulations do provide pain relief, there is sometimes significant burning and nausea associated with the oral administration of capsaicin. In light of the many disorders of the oral cavity and pharynx which cause pain, it would be quite useful to have an oral capsaicin formulation that minimizes these side effects.

Therefore, it is an object of the present invention to provide a composition and method for the oral delivery of capsaicin, or derivatives, or analogs thereof which decreases the initial burning and nausea associated with the oral administration of the active compound, yet which provides analgesia for oral or pharynx pain.

It is another object of the present invention to provide a composition and method for the oral delivery of capsaicin, derivatives, or analogs thereof which soothes and relieves oral or pharynx pain.

SUMMARY OF THE INVENTION

Methods and compositions are provided for the oral delivery of temporally increasing concentrations of capsaicin, its derivatives, and analogs, including natural substances such as paprika and red pepper (collectively referred to as "capsaicinoids"), to provide oral and pharyngeal analgesia while minimizing the sensations of nausea and burning associated with the oral administration of capsaicinoids. The methods and compositions described herein soothe and relieve oral or pharynx pain.

The composition includes one or more capsaicinoids dispersed within a solid carrier material such as a lollipop, with successively decreasing concentrations of capsaicin from the center out to the periphery. Other examples of solid formulations include a tablet, caplet, lozenge, troche, pill, candy, popsicle, or similar formulation. The formulation is designed in such a manner that the outer layer contains a concentration of one or more capsaicinoids which does not cause significant nausea or mouth burn, yet is sufficient to desensitize the patient to nausea or mouth burn associated with exposure to an increased concentration of capsaicinoid in the next inner layer. The patient is thus exposed to increasing concentrations of capsaicin as he is simultaneously becoming desensitized to its uncomfortable effects. When designed optimally, the patient is not, or is only minimally aware of the desensitization.

The capsaicinoids include all those mentioned in the Background of the Invention, including, for example, capsaicin, dihydrocapsaicin, norhydrocapsaicin, homocapsaicin, homodihydrocapsaicin I, norhydrocapsaicin, homodihydrocapsaicin, and nordihydrocapsaicin, civamide, nonivamide, NE-19550 (also called olvanil, N-[4-hydroxy-3-methoxyphenyl) methyl]-9Z-octadecenamide)), NE-21610 (N-[(4-(2-aminoethoxy)-3-methoxyphenyl) methyl]-9Z-octadecenamide) (Sandoz Pharmaceutical Corp. East Hanover, N.J.) (Chemical Abstract Service Registry No. 118 090 17 8), and NE-28345 (also called N-oleyl-homovanillamide, formally named N-(9Z-octadecenyl)-3-methoxy-4-hydroxyphenylacetamide) (Chemical Abstract Service Registry No. 107 512 56 1). (NE-19550, NE-21610, and NE-28345 are discussed in Dray, A., et al., "NE-19550 and NE-21610, antinociceptive capsaicin analogues; studies on nociceptive fibres of the neonatal rat tail in vitro," *Eur. J. Pharmacol.* (Netherlands), vol. 181, no. 3, pp. 289–293 (Jun. 8, 1990), and Brand, L. M., et al., "Anti-inflammatory pharmacology and mechanism of the orally active capsaicin analogs, NE-19550 and NE-28345," *Agents Actions* (Switzerland), vol. 31, nos. 3–4, pp. 329–340 (November 1990)).

BRIEF DESCRIPTION OF THE DRAWINGS

One of the thirteen subjects had no relief of pain. The third bar shows the average peak pain intensity (3.41±3.82) after that one subject's data was removed from the set.

Patients were followed for two hours after consumption of the applicator and based on that time interval, the mean duration of analgesia was 98.75±33.5 minutes. Many individuals reported pain relief beyond two hours, and because they were not available to measure pain intensity, it was not feasible to accurately calculate the true analgesic duration.

DETAILED DESCRIPTION OF THE INVENTION

Methods and compositions are provided for the oral delivery of temporally increasing concentrations of capsaicin, its derivatives, and analogs, to provide oral or pharyngeal analgesia while minimizing sensations of nausea and burning associated with the oral administration of capsaicinoids. The methods and compositions described herein soothe and relieve oral or pharynx pain.

Indications which may be treated by the compositions and methods of the present invention include all inflammatory and neuropathic pain conditions involving the oral cavity, the oral pharynx, and other painful mucosal pathology along the course of the gastro-intestinal tract. Specific pain indications treatable by the methods and compositions of the present invention include pain associated with tonsillopharyngitis, mucositis, oral surgery, cancer, dental procedures or problems, gum disease, tooth loss or growth, oral or pharyngeal infections, general mouth pain or discomfort, pain in the abdomen, and headaches.

The capsaicinoids are distributed within a solid or a gel material, with successively decreasing concentrations of capsaicinoids from the center of the material to the periphery, either in a discrete, or a continuous concentration gradient, or both. The concentration gradient is such that the outer layer exposes the patient to a concentration of one or more capsaicinoids which does not cause significant nausea or mouth burn, and is sufficient to desensitize the patient to the nausea or mouth burn associated with exposure to the increased concentration of capsaicinoid(s) in the next inner layer.

In one embodiment, capsaicin, a derivative, or analog, or a natural substance that includes a capsaicinoid, such as paprika or red pepper, or a mixture thereof, is dispersed within a lollipop, with successively decreasing concentrations of capsaicin from the center out to the periphery. The lollipop is administered to a patient in need of amelioration of oral or pharynx pain. Alternatively, the capsaicinoid can be dispersed, with decreasing concentrations from the center to the periphery, in a tablet, caplet, lozenge, troche, pill, candy, gel vehicle, or similar formulation.

According to the invention, the composition can have two or more gradient layers. In one embodiment, the composition has four to 8 layers. Each layer is of any desired thickness, and can have differing thicknesses within the same formulation. The concentration of the active ingredient in the outer layer should be determined empirically to be that concentration that promotes desensitization without inducing significant mouth burn. The inner layer should contain a concentration of active ingredient that provides a desired level of desensitization. Typically, concentrations of the active ingredient in the outer layer range between 0.25% and 0.5% of a capsaicinoid, or 2 to 5 mg. Typically, the concentration of capsaicinoid in the outer layer is 0.25%. The inner layer typically will have a 1.5% to 2% concentration of capsaicinoid, or 2 to 5 mg. In one embodiment, the inner layer has a concentration of 2% by weight of capsaicinoid, and a weight of 10 mg. In one embodiment the capsaicinoid is dispersed in layers ranging in thickness from 6 mm to 10 mm, and the concentration of capsaicinoids ranges from 0.25% in the outer layer to 2% in the inmost layer. In one embodiment, the concentration steps from the outermost to the inmost layer are from 0.25%, 0.5%, 1%, 1.5%, and 2%. A preferred thickness of each layer ranges from 3 to 6 mm.

I. Active Ingredient

Capsaicinoids include all those compounds mentioned in the Background of the Invention, including, for example, dihydrocapsaicin, norhydrocapsaicin, homocapsaicin, homodihydrocapsaicin I, norhydrocapsaicin, homodihydrocapsaicin, and nordihydrocapsaicin, civamide, nonivamide, NE-19550 (also called olvanil, N-[4-hydroxy-3-methoxyphenyl)methyl]-9Z-octadecenamide)), NE-21610 (N-[(4-(2-aminoethoxy)-3-methoxyphenyl) methyl]-9Z-octadecenamide) (Sandoz Pharmaceutical Corp. East Hanover, N.J.) (Chemical Abstract Service Registry No. 118 090 17 8, and NE-28345 (also called N-oleyl-homovanillamide, formally named N-(9Z-octadecenyl)-3-methoxy-4-hydroxyphenylacetamide) (Chemical Abstract Service Registry No. 107 512 56 1). (NE-19550, NE-21610, and NE-28345 are discussed in Dray, A., et al., "NE-19550 and NE-21610, antinociceptive capsaicin analogues; studies on nociceptive fibres of the neonatal rat tail in vitro," *Eur. J. Pharmacol.* (Netherlands), vol. 181, no. 3, pp. 289–293 (Jun. 8, 1990), and Brand, L. M., et al., "Anti-inflammatory pharmacology and mechanism of the orally active capsaicin analogs, NE-19550 and NE-28345," *Agents Actions* (Switzerland), vol. 31, nos. 3–4, pp. 329–340 (November 1990)).

Non-limiting examples of capsaicinoids useful in the present method and compositions include those described in E.P.A. No. 0 149 545 filed by the Procter & Gamble Co., and published on 24 Jul. 1986. These are of the general formula:

wherein $R_1$ is OH or $OCH_3$, $R_2$ is OH or $OC(O)R_3$, $R_3$ is selected from $C_1$–$C_4$ alkyl, phenyl and methyl, X is NHC (O), NHC(O)O, NHC(O)NH, NHC(S)NH, C(O)NH, or NH(O)S(O), and R is a $C_5$–$C_{23}$ alkyl, $C_5$–$C_{11}$ alkenyl, $C_{11}$–$C_{23}$ cis alkenyl, $C_{11}$–$C_{23}$ alkynyl, $C_{11}$–$C_{23}$ alkadienyl, or $C_{11}$–$C_{23}$ (methylene substituted) alkane. For purposes of this application, "methylene substituted alkane" means one in which the two hydrogens attached to a carbon atom have been replaced by the bivalent radical $=CH_2$.

Specific embodiments of the compounds described herein include those wherein both $R_1$, and $R_2$ are OH and X is C(O)ONH or NHC (O); and those wherein $R_1$, is $OCH_3$, $R_2$ is OH or $R_3CO$ and X is C(O)NH, NHC(O) or NHC(S)NH.

Embodiments of the compounds described herein include those in which the R groups include $C_7$–$C_{10}$ alkyls and trans alkenyls, and $C_{16}$–$C_{21}$ cis alkenyls and alkadienyls. Moieties within these groups include —$C_8H_{17}$, —$C_9H_{17}$ and —$C_{17}H_{33}$. Capsaicin analogs include N-vanillyl-alkadienamides, N-vanillyl-alkanedienyls, and N-vanillyl-cis-monounsaturated alkenamides. A specific capsaicinoid is N-vanillyl-9E-octadecenamide (N-vanillyloleamide).

Examples of capsaicin analogs and methods for their preparation are described in the following patents and patent applications, all incorporated by reference herein: Capsaicin (8-methyl-N-vanillyl-6E-nonenamide) and "synthetic" capsaicin (N-vanillylnonanamide) are disclosed as analgesics in U.S. Pat. No. 4,313,958, to T. R. LaHann, issued Feb. 2, 1982. European Patent Application 0 089 710, to the Procter & Gamble Co., (inventors T. R. LaHann and B. L. Buckwalter), published Sep. 28, 1983, describes hydroxyphenylacetamides with analgesic and anti-irritant activity. Similarly, analgesic and anti-irritant activity is disclosed for N-vanillylsulfonamides in European Patent Application 0 068 591, by the Procter & Gamble Co. (inventors B. L. Buckwalter and T. R. LaHann), published Jan. 5, 1983; N-vanillylureas in European Patent Application 0 068 590, et al., by the Procter & Gamble Co., (inventors B. L. Buckwalter and T. R. LaHann) published Jan. 5, 1983; N-vanillylcarbamates in European Patent Application 0 068 592 (inventors B. L. Buckwalter and T. R. LaHann), published Jan. 5, 1983; N-[(substituted phenyl)methyl] alkynylamides in U.S. Pat. No. 4,532,139, issued Jul. 30, 1985 to J. M. Janusz and T. R. LaHann; methylene substituted-N-C (substituted phenyl)methyl]-alkanamides in U.S. Pat. No. 4,544,668 to B. L. Buckwalter, J. M. Janusz, and T. R. LaHann, issued Oct. 1, 1985; N[(substituted phenyl)methyl]-cis-monounsaturated alkenamides in U.S. Pat. No. 4,564,633 to B. L. Buckwalter and T. R. LaHann, issued Jan. 14, 1986; and N-[(substituted phenyl)methyl]-diunsaturated amides in U.S. Pat. No. 4,544,669 to B. L. Buckwalter, J. M. Janusz, and T. R. LaHann, issued Oct. 10, 1985. Also incorporated by reference herein are N-phenylmethylalkenamide capsaicin derivatives described in U.S. Pat. Nos. 4,493,848 to T. R. LaHann and B. L. Buckwalter, issued Jan. 15, 1985; 4,532,139 to J. M. Janusz and T. R. LaHann, issued Jul. 30, 1985; 4,564,633 to T. R. LaHann and B. L. Buckwalter, issued Jan. 14, 1986; 4,544,668 to J. M. Janusz, B. L. Buckwalter, and T. R. LaHann, issued Oct. 1, 1985; 4,544,669 to T. R. LaHann, J. M. Janusz, and B. L. Buckwalter, issued Oct. 1, 1985.

Capsaicin can be isolated from capsicum fruits by methods known to those of ordinary skill in the art, including ethanol extraction from capsicum frutescens or capsicum annum. See, e.g., J. C. Thresh, "Capsaicin, the Active Principle of Capsicum Fruits," p. 21, *The Pharmaceutical Journal and Transaction* (Jul. 8, 1876). Alternatively, capsaicin may be synthesized by methods known to those of ordinary skill in the art. See, e.g., L. Crombie, et al., "Amides of Vegetable Origin. Part VI. Synthesis of Capsaicin.", *Journal of the Chemical Society*, pp. 1025–1027 (1955); O.P. Vig, et al., "A New Synthesis of N-(4'-Hydroxy-3'-methoxybenzyl)-8-methyl-non-6(E)-enamide (Capsaicin)," *Indian Journal of Chemistry*, vol. 17B, pp. 558–559 (June 1979); G. T. Walker, "Capsaicin: Properties, reactions and uses," *Manufacturing Chemist and Aerosol News*, pp. 35–36, 42 (June 1968).

II. Oral Delivery Formulations

Oral delivery formulations include solids or gels, including, but not limited to, tablets, caplets, lozenges, troches, pills, and candies, such as lollipops. These may be formulated by methods well-known to those skilled in the art. The following publications, all incorporated herein by reference, describe methods of production of candy useful for the method and compositions described herein: *Manufacturing Confectioner* (monthly publication) (Manufacturer Confectioner Publishing Co., Glen Rock, N.J. 07452 1956-present), *Confectionery Production* (monthly publication) (Specialized Publications Ltd., Surbiton, Surrey KT6 4BT Eng.), Walter L. Richmond, *Candy Production: Methods and Formulas* (Manufacturing Confectioner Publishing Co. Chicago, Ill. 1948), Stroud Jordan, *Confectionery Problems* (National Confectioner's Association Chicago, Ill. 1930), *Encyclopedia Britannica*, 15th edition, vol. 19, pp. 394–397, 406 (Chicago 1992), *The Encyclopedia Americana*, vol. 5, pp. 538–539 (Grolier Inc. Danbury, CT 1992), and Jan Morgan, *Chocolate and Candy Cookbook* (Arco Publishing, Inc. New York 1983).

The following publications, incorporated by reference herein, describe standard methods of production of tablets, caplets, lozenges, troches, and pills, useful for the methods and compositions described herein: Howard C. Ansel, et al., eds., *Pharmaceutical Dosage Forms and Drug Delivery Systems*, 6th edition (Williams & Wilkins Malvern, N.J. 1995) (esp. chapter 3, pp. 78–80, and chapter 5, pp. 164–223); and *Encyclopedia Britannica*, 15th edition, vol. 21, pp. 321–322, 383 (Chicago 1992).

Pills, Tablets, and Lozenges

Pills, tablets, lozenges and the like can be prepared by methods known to those of ordinary skill in the art. Described below are standard preparation techniques, including methods by which multi-layer pills, tablets, and lozenges may be prepared. These pills, tablets, and lozenges are prepared according to the methods of the present invention by incorporating successively decreasing concentrations of one or more capsaicinoids from the center to the periphery of the formulation. This provides oral and pharyngeal analgesia to a patient in need thereof, while minimizing the sensations of nausea and burning associated with the oral administration of capsaicinoids.

The capsaicinoids can be provided in natural form, such as ground or dry fruit, i.e., red pepper or paprika, or can be provided in isolated or purified form, or in the form of a synthetic derivative.

Pills.

Before the machine-made compressed tablet, pills were a very popular solid dosage form, being prepared at the dispensing bench by the pharmacist. Today pills are rarely prescribed, though some popular types are manufactured by machine. The powdered ingredients are mixed together with a binding agent, such as acacia or tragacanth, and are then made into a plastic mass by incorporation of any liquid drugs and addition of an inert liquid. The resulting mass, known as a pill mass, is then rolled into spheres and coated with talc, gelatin, or sugar.

Tablets.

Tablets, by far the most common method of administration of drugs, are only rarely made by compression of the drug alone (e.g., potassium bromide tablets). Usually, the drug is mixed with suitable diluents, such as dextrin, lactose, salt, starch, or synthetic substances, designed to ensure disintegration of the tablet in the body. To prevent sticking in the machine, a lubricant such as liquid paraffin, stearic acid, talc, or a synthetic substance is usually added. Furthermore, it is essential that the tablet machines are fed with the drug mixture in a free-flowing form to ensure complete filling of the molds. To achieve this, the drug mixture is customarily granulated by mechanically forcing pellets of the mixture through a sheet of perforated metal. The granulated mixture is fed into the tablet machine, which feeds the correct dose into a cavity, the mixture then being compressed by means of a punch that fits into the cavity. To be successful, the tablet maker must choose correct diluents and lubricants, prepare suitable granules, and obtain the right degree of compression in the tablet machine. Excessive compression may mean that the tablet will not disintegrate in the body; insufficient compression results in fragile tablets that may break, causing inaccurate dosage. Coatings of various types may be applied to the tablet—to protect the ingredients from deterioration, to hide the taste of certain drugs, to control the release of the drug from the tablet, or to produce a more attractive tablet. For sugar coatings, a concentrated sucrose syrup containing suspended starch, calcium or magnesium carbonate, or other suitable substance is applied, each successive layer being dried before the application of the next. After the final layer is dried, it is highly polished to give an elegant finish. Sugar coatings provide both protection and a sweet taste. The chief drawback to sugar coating is the long time involved. This led to the development of film coating, in which a very thin transparent film, usually a cellulose derivative, is applied. Enteric coating is designed to resist solution in the stomach and to dissolve int eh more alkaline intestinal fluid. Many substances have been used for enteric coatings, one of the more recent being cellulose acetate phthalate (cellacephate). In the manufacture of layered tablets, incorporating two or more drugs, a compressed tablet is fed to a second machine where another layer is compressed around it. In this way, drugs normally incompatible may be formulated in the same tablet.

Other solid dosages.

Troches, also known as lozenges or pastilles, disintegrate or dissolve in the mouth, slowly releasing the active drug. The base usually consists of a mixture of sugar and gum or gelatin. Lozenges are generally manufactured by compression techniques, while pastilles are fabricated by fusion and the use of molds. Dry extracts are prepared by the methods described above for fluid extracts, followed by evaporation, usually under reduced pressure, either to a pilular consistency or to dryness. Dry extracts are usually granulated by being passed through a sieve and may be used for the preparation of tablets.

The compositions described herein can include other optional ingredients such as stabilizers, thickeners, surface active agents, conditioners and flavorants, provided that these optional ingredients are orally-consumable, non-toxic and acceptable as to taste characteristics. Stabilizer compounds include preservatives, e.g., sodium chloride, antioxidants, e.g., calcium and sodium ascorbate, ascorbic acid, butylated hydroxy-anisole (mixture of 2- and 3-tertiary-butyl-4-hydroxy-anisole), butylated hydroxy toluene (w,6-di-tertiary-butyl-4-methyl phenol), propyl gallate and the like and sequestrants, e.g. citric acid.

Thickener compounds include carriers, binders, protective colloids, suspending agents, emulsifiers and the like, e.g., agar, carrageenan; cellulose and cellulose derivatives such as carboxymethyl cellulose and methyl cellulose; natural and synthetic gums such as gum arabic, gum tragacanth; gelatin, proteinaceous materials; lipids; carbohydrates; starches, pectins, and emulsifiers, e.g., mono- and diglycerides of fatty acid, skim milk powder, hexoses, pentoses, disaccharides, e.g., sucrose corn syrup and the like.

Surface active agents include emulsifying agents, e.g., fatty acids such as capric acid, caprylic acid, palmitic acid, myristic acid and the like, mono- and diglycerides of fatty acids, lecithin, defoaming and flavor-dispersing agents such as sorbitan monostearate, potassium stearate, hydrogenated tallow alcohol and the like.

Conditioners include compounds such as bleaching and maturing agents, e.g., benzoyl peroxide, calcium peroxide, hydrogen peroxide and the like, starch modifiers such as peracetic acid, sodium chlorite, sodium hypochlorite, propylene oxide, succinic anhydride and the like, buffers and neutralizing agents, e.g., sodium acetate, ammonium bicarbonate, ammonium phosphate, citric acid, lactic acid, vinegar and the like; colorants, e.g., carminic acid, cochineal, tumeric and curcuma and the like; firming agents such as aluminum sodium sulfate, calcium chloride and calcium gluconate; texturizers, anti-caking agents, e.g., aluminum calcium sulfate and tribasic calcium phosphate; enzymes; yeast foods, e.g., calcium lactate and calcium sulfate; nutrient supplements, e.g., iron salts such as ferric phosphate, ferrous gluconate and the like riboflavin, vitamins, zinc sources such as zinc chloride, zinc sulfate and the like.

Other flavorants and flavor intensifiers include organic acids, e.g., acetic acid, formic acid, 2-hexenoic acid, benzoic, acid, n-butyric acid, caproic acid, caprylic acid, cinnamic acid, isobutyric acid, isovaleric acid, alpha-methyl-butyric acid, propionic acid, valeric acid, 2-methyl-2-pentenoic acid, and 2-methyl-3-pentenoic acid; ketones and aldehydes, e.g., acetaldehyde, acetophenone, acetone, acetyl methyl carbinol, acrolein, n-butanal, crotonal, diacetyl, 2-methyl butanal, beta-dimethylacrolein, methyl-n-amyl ketone, n-hexenal, 2-hexenal, isopentanal, hydrocinnamic aldehyde, cis-3-hexenal, 2-heptenal, nonyl aldehyde, 4-(p-hydroxy-phenyl)-2-butanone, alpha-ionone, beta-ionone, methyl-3-butanone, benzaldehyde, damascone, damascenone, acetophenone, 2-heptanone, o-hydroxyacetophenone, 2-methyl-2-hepten-6-one, 2-octanone, 2-undecanone, 3-phenyl-4-pentenal, 2-phenyl-2-hexenal, connamaldehyde, beta-cyclohomocitral, 2-pentanone, 2-pentenal and propanal; alcohols such as 1-butanol, benzyl alcohol, 1-borneol, trans-2-buten-1-ol, ethanol, geraniol, 1-hexanal, 2-heptanol, trans-2-hexenol-1, cis-3-hexen-1ol, 3-methyl-3-buten-1-ol, 1-pentanol, 1-penten-3-ol, p-hydroxyphenyl-2-ethanol, isoamyl alcohol, isofenchyl alcohol, phenyl-2-ethanol, alpha-terpineol, cis-terpineol hydrate, eugenol, linalool, 2-heptanol, acetoin; esters, such as butyl acetate, ethyl acetate, ethyl acetoacetate, ethyl benzoate, ethyl butyrate, ethyl caprate, ethyl caproate, ethyl caprylate, ethyl cinnamate, ethyl crotonate, ethyl isobutyrate, ethyl isovalerate, ethyl laurate, ethyl myristate, ethyl alpha-methylbuytrate, ethyl propionate, ethyl salicylate, trans-2-hexenyl acetate, hexyl acetate, 2-hexenyl butyrate, hexyl butyrate, isoamyl acetate, isopropyl butyrate, methyl acetate, methyl butyrate, methyl caproate, methyl isobutyrate, alpha-methylphenylglycidate, ethyl succinate, isobutyl cinnamate, cinnamyl formate, methyl cinnamate and terpenyl acetate; terpene hydrocarbons such as myrcene, caryophyllene, 1-phellandrene, p-cymene, 1-alpha-pinene, beta-pinene, dihydrocarveol; pyrazines such as 2,3-dimethylpyrazine, 2,5-dimethylpyrazine, 2,6-dimethyl-pryrazine, 3-ethyl-2,5-dimethylpyrazine, 2-ethyl-3,5,6-trimethylpyrazine, 3-isomoamyl-2,5-dimethylpyrazine, 5-isoamyl-2,3-dimethylpyrazine, 2-isoamyl-3,5,6-trimethylpyrazine, isopropyl dimethylpyrazine, methyl ethylpyrazine, tetramethylpyrazine, tremethylpyrazine; essential oils and extracts such as jasmine absolute, cassia oil, cinnamon bark oil, rose absolute, orris absolute, oil of cubeb, oil of coriander, oil of pimento leaf, oil of patchouli, oil of nutmeg, lemon oil, safron oil, Bulgarian rose, yara yara and vanilla; lactones such as gamma-nonalactone; sulfides, e.g., methyl sulfide and other materials such as maltol, acetoin and acetals (e.g., 1,1-diethoxyethane, 1,1-dimethoxyethane and dimethoxymethane), and piperidine.

Candy

Multilayer candy, including chocolate, can be prepared by methods known to those of ordinary skill in the art. The references cited herein describe standard techniques for the manufacture of candy. This candy is prepared according to the methods of the present invention by incorporating successively decreasing concentrations of one or more capsaicinoids from the center to the periphery of the candy. This provides oral and pharyngeal analgesia to a patient in need thereof, while minimizing the sensations of nausea and burning associated with the oral administration of capsaicinoids. The capsaicinoids can be provided in natural form, i.e., red pepper or paprika, or can be provided further isolated and purified, or provided in synthetic form.

The capsaicin formulation can optionally include other ingredients such as analgesics (phenol or lidocaine (2-(diethylamino)-N-(2,6-dimethyl-phenyl) acetamide), sweeteners, flavorings, and agents to prevent nausea).

Methods of Administration

In one embodiment of the method described herein, the compositions described herein are administered up to four to five times daily to a patient in need of relief from oral or pharyngeal pain. In one embodiment, the patient takes approximately 15 minutes to consume the lollipop.

In one embodiment of the applicator, the concentration of red pepper in each layer varies from 0.25% to 2% by weight, or 1.5 mg to 18 mg. The thickness of each layer ranges from 0.6 cm to 3.5 cm. Typical numbers of layers within the applicator are between 3 to 10.

EXAMPLE 1

Incorporation of Cayenne Pepper into a Lollipop with Decreasing Concentrations of Pepper Toward the Periphery Construction of the Lollipops The inner layer was constructed first. Thirty-six grams of Guittard Candy Wafers, Guittard Co., 10 Guittard Rd., Burlingame, Calif. 94011, were placed in a microwave (Menumaster™, Model No. FS-10EVP, 600 East 54th Street North, Sioux Falls, SD 57104) on high for about 30 seconds, and then for another 10 seconds. The candy wafers were soft candy chips consisting of sugar, vegetable shortening, whey and nonfat milk. The melted candy was stirred until evenly smooth, and then 0.36 grams of red cayenne pepper (McCormick Co.) were added (approximately 1% by weight) After uniform mixing, 2 grams of candy were weighed into a standard mold (the mold was placed on the scale and the amount weighed into the mold). After weighing out 18 inner layer molds, the mold was placed in a freezer for about 10 minutes to harden. While the inner layer was hardening, the middle layer was constructed. Thirty-six grams of candy were placed in the microwave as above. Cayenne pepper (0.18 grams) were added, and after mixing, 3 grams of candy-pepper mixture were weighed into a total of 12 molds (approximately 0.5% by weight). The hardened inner layer was pressed in the center of the soft middle layer, and the middle layer mold was placed in the freezer for 10 minutes to harden. The outer layer was then constructed by placing 32 grams of candy in the microwave as above, and adding 0.08 grams cayenne pepper (approximately 0.25% by weight). After weighing 4 grams of candy-pepper mixture into a total of 8 molds, the middle layer (now containing the inner layer) was inserted into the soft outer layer molds. The mold, now containing all three layers, was placed in the microwave on high for two 20 second time periods, to soften all three layers. The lollipop sticks (CK South, 3375 Medlock Bridge Rd., Norcross, Ga. 30092) were inserted in the molds, and the molds are placed again in the freezer for 15 minutes to harden. This made one-half of the lollipop. The remaining half was constructed in the same manner as described above, except instead of placing the lollipop sticks in, the half containing the stick was placed on top of the softened three-layered other half. The complete lollipop was then placed in the freezer for 15 minutes to harden. After hardening, the lollipops were wrapped in cellophane. Table I presents a basic recipe for making lollipops of the size used in the study ("study size"), and a slightly smaller size ("small size"). Table II presents the mold sizes for three-layer lollipops and four-layer lollipops.

TABLE I

Recipe for Lollipops

| | Candy (g) | Pepper (g) | % Pepper |
|---|---|---|---|
| (study size) | | | |
| Inner Layer | 2 | 0.02 | 1.0% |
| Middle Layer | 4 | 0.02 | 0.5% |
| Outer Layer | 8 | 0.02 | 0.25% |
| (small size) | | | |
| Inner Layer | 2 | 0.02 | 1.0% |
| Middle Layer | 3 | 0.015 | 0.5% |
| Outer Layer | 4 | 0.01 | 0.25% |

TABLE II

| Mold sizes for small three-layer lollipops (diameters): | |
|---|---|
| Inner Layer | (¾ inch) |
| Middle Layer | (⅞ inch) |
| Outer Layer | (1⅛ inch) |
| Exemplary mold size for four-layer lollipops (diameters): | |
| Inner Layer | (1/2 inch) |
| Inner-Most Middle Layer | (¾ inch) |
| Outer-Most Middle Layer | (⅞ inch) |
| Outer Layer | (1⅛ inch) |

The basic recipe for the lollipop is 20 grams Guittard Wafers and 0.2 grams Red Cayenne Pepper, approximately 1% by weight.

EXAMPLE 2

Administration of Lollipops Containing Cayenne Pepper to Patients

Research Design and Methods

Three-layer study-size lollipops containing cayenne pepper were constructed as above. Patients were screened initially by telephone. Pain and nasal congestion were assessed via a category scale and ability to breathe with mouth closed. The category scale for nasal congestion was: no congestion; mild congestion; moderate congestion; or severe congestion. The category scale for pain was: no pain; mild pain; moderate pain; or severe pain. Patients with moderate to severe pain, and no significant nasal congestion, were invited to the clinical center for a face-to-face screening. Each patient was then asked to rate his or her spontaneous pain, pain on swallowing and intensity of swelling sensation of the throat on a visual analogue scale. (Schachtel, B. P., et al., "Rating scales for analgesics in sore throat," Clin. Pharmacol. Ther., 1984;36;151–6). A score of $\geq 55$ mm on a 100-mm visual analog scale in one of these categories was necessary for admission to the study. (Schachtel, B. P., "Sore Throat Pain," in Max, M. B., et al., eds., Advances in Pain Research and Therapy: The Design of Analgesic Clinical Trials, 18;393–407 (New York: Raven Press Ltd., 1991). The subject was asked to breathe through the nose for two minutes with the mouth closed to assess for severity of nasal congestion. If there was no significant impediment to breathing, then the pharynx was examined for objective evidence of tonsillopharyngitis using the rating scale presented in Schachtel, B. P., et al., "Subjective and objective features of sore throat," *Arch. Intern. Med.*, 1984:144;497–500, incorporated herein by reference. A score of 4 or more on the 12-point tonsillopharyngitis index was required to participate. If the subject passed inclusion and exclusion criteria, he or she was invited to participate in the study.

Once the patients were screened and consent obtained, they were admitted to the outpatient section of the general clinical research center (GCRC). The admitting nurse collected vital signs, administers the pain assessment measures, and administered the capsaicin applicator. The patients were instructed to suck and lick the applicator until it had completely dissolved within 20 minutes or until aversive side-effects developed, i.e., nausea, intolerable or severe mouth-burn or throat-burn. During consumption of the applicator, the nurse assessed pain intensity and relief every 5 minutes. After completion of the applicator, the nurse assessed pain intensity and relief every 15 minutes, for a total of 12 measurements during and after consumption. In addition, pleasantness or unpleasantness scales were administered to the subjects immediately after completion of the applicator, and 3 hours later. If pain relief was experienced, the patients were instructed to telephone the GCRC nurse to report when pain returned.

Biostatistical Design and Analysis

For purposes of this study, a clinically significant response was a 55 unit decrease in pain intensity relative to baseline estimations. This was a conservative response threshold when compared to efficacy studies of aspirin with caffeine in patients with tonsillopharyngitis. (Schachtel, B. P., et al., "Sore throat pain in the evaluation of mild analgesics," *Clin. Pharmacol. Ther.*, 1988:44;707–11; Schachtel, B. P., et al., "Caffeine as an analgesic adjuvant: a double-blind study comparing aspirin 800 mg with caffeine 64 mg to aspirin 800 mg and placebo in patients with sore throat," *Arch. Intern. Med.*, 1991:151;733–737). A phase-II, two stage Simon's design was used to determine the efficacy of the treatment. (Simon, R., "Optimal two-stage designs for phase II clinical trials," *Controlled Clinical Trials*, 1989:10;1–10.) A minimum response probability (p0) of 0.6 has been chosen for this study. If the response rate is less than p0, the probability of declaring that the treatment will be effective in future studies (controlled trials) would be 0.05. If the true response rate is greater than 0.8 (p1), the probability of rejecting the treatment for further studies would be less than 0.10.

| | | Two stage Simon's Design | |
|---|---|---|---|
| | | reject treatment if response rate less than or equal p0 | |
| p0 | p1 | state I r1/n1 | stage II r2/n2 |
| 0.6 | 0.8 | 12/19 | 37/53 |

The data was analyzed using ANOVA (SAS Institute Inc., SAS Users Guide: Statistics, Version 3 Addition, Cary, N. C., 1985) with repeated measures for the primary outcome measure (pain intensity reduction) and the study continues if the response rate is greater than 0.6. Data are analyzed in a similar manner on completion of stage II, assuming state I criteria have been satisfied.

Results of Stage I

Figure 1:
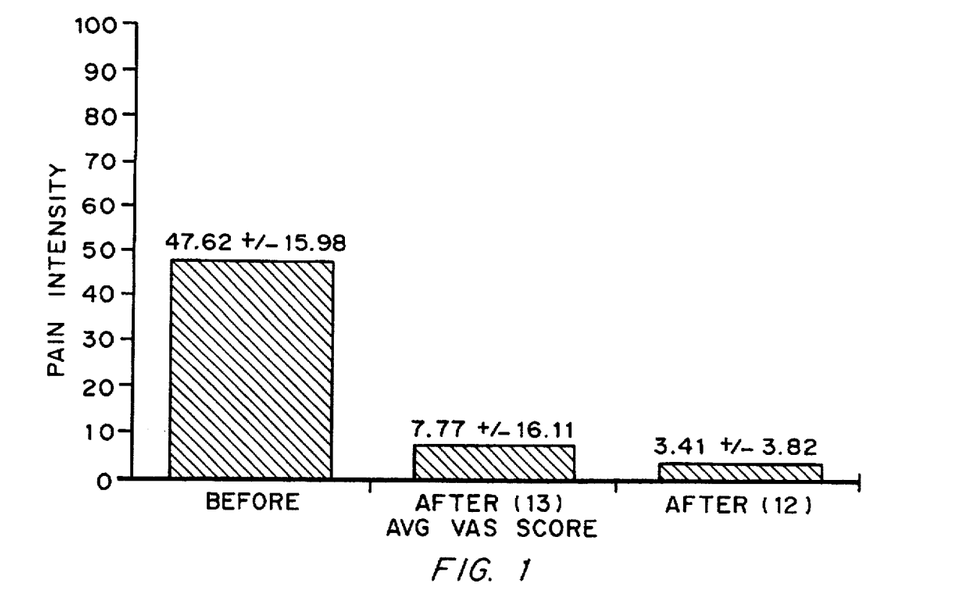
FIG. 1 (average peak pain relief) is a bar chart graph, in which the ordinate is in visual analog scale units of reduction in pain intensity, and the abscissa indicates whether the measurements are before or after consumption of a three-layer lollipop (applicator). The subjects were presented a horizontal line measuring 100 mm in length. The line was anchored at either end with the term "no pain" and "most intense pain imaginable". The bars in the figures represent mean pain intensity before and after consumption of the lollipop. The numbers at the top of the bars indicate the mean ± standard deviation values for pain intensity. The first bar shows the average spontaneous pain intensity (47.62±15.98) in thirteen subjects prior to consuming the lollipop. The middle bar shows the average peak pain intensity after each subject consumed the lollipop.
Figure 2:
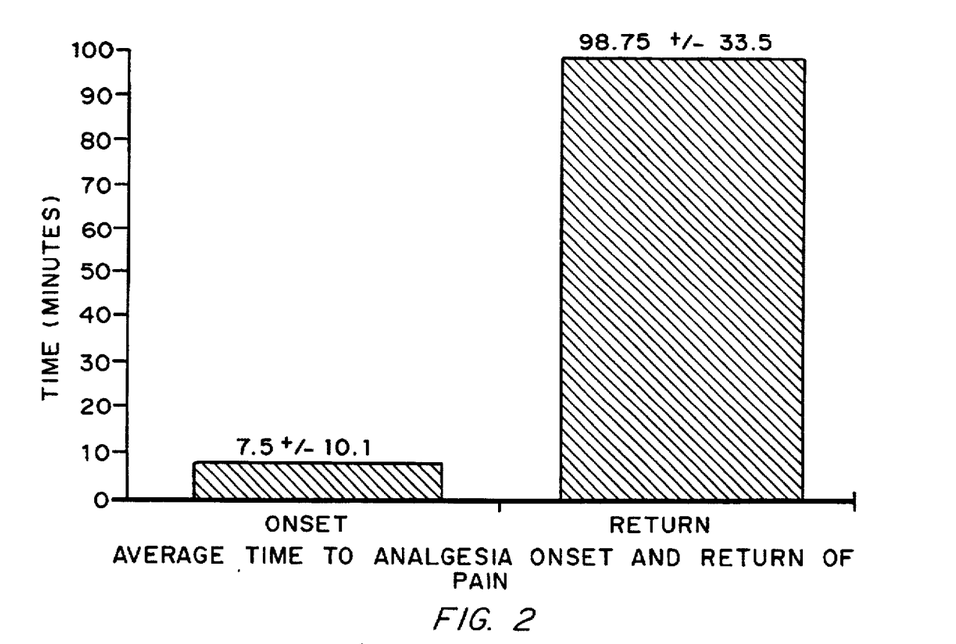
FIG. 2 is a bar chart graph of the time in minutes, before onset of analgesia, and the return of pain after consumption of the three-layer lollipop (applicator). The analgesic onset is defined as the time period to 50% reduction in pain. Duration is defined as the time period to return to baseline. The mean onset of analgesia was 7.5 minutes ±10.1 (s.d.)

The results of Stage I are shown in FIG. 1 and FIG. 2. FIG. 1 (average peak pain relief) is a bar chart graph, in which the ordinate is in visual analog scale units of reduction in pain intensity, and the abscissa indicates that the measurements are before and after consumption of a three-layer lollipop (applicator). The subjects were presented a horizontal line measuring 100 mm in length. The line was anchored at either end with the term "no pain" and "most intense pain imaginable". The bars in the figures represent mean pain intensity before and after consumption of the lollipop. The numbers at the tops of the bars indicate the mean ± standard deviation values for pain intensity. The first bar shows the average spontaneous pain intensity (47.62±15.98) in thirteen subjects prior to consuming the lollipop. The middle bar shows the average peak pain intensity after each subject consumed the lollipop.

One of the thirteen subjects had no relief of pain. The third bar shows the average peak pain intensity (3.41±3.82) after that one subject's data was removed from the set.

FIG. 2 is a bar chart graph of the time in minutes, before onset of analgesia, and the return of pain after consumption of the three-layer lollipop (applicator). The analgesic onset is defined as the time period to 50% reduction in pain. Duration is defined as the time period to return to baseline. The mean onset of analgesia was 7.5 minutes ±10.1 (s.d.) Patients were followed for two hours after consumption of the applicator and based on that time interval, the mean duration of analgesia was 98.75±33.5 minutes. Many individuals reported pain relief beyond two hours, and because they were not available to measure pain intensity, it was not feasible to accurately calculate the true analgesic duration.

The first study conducted used homogeneous lollipops, and the second used a graded release lollipops. In both studies, unpleasantness was measured on a visual analog scale measuring from 0 mm to 100 mm. The ends of the visual analog scale were anchored to the left with the words "no unpleasantness," and to the right with the words "the most unpleasant sensation imaginable." In the first study, the unpleasantness scores were always above the 80 mm level. In the second studies, scores averaged below the 50 mm level, and some patients found the lollipops to be pleasant. The studies suggest that graded release of capsaicin reduces the incidence and severity of side effects of oral administration of capsaicin, such as nausea and mouth burn.

Modifications and variations of the methods and compositions described herein will be obvious to those skilled in the art from the foregoing detailed description and are intended to come within the scope of the appended claims.

I claim:

1. A composition for the oral delivery of temporally increasing concentrations of one or more capsaicinoids to provide oral or pharyngeal analgesia, wherein the composition comprises one or more capsaicinoids dispersed in a solid or gel vehicle in which the concentration of the capsaicinoid(s) decreases from the center toward the periphery of the vehicle.

2. The composition of claim 1 which contains at least two discrete layers, and wherein the outer layer contains a concentration of one or more capsaicinoids which does not cause significant nausea or mouth burn, and is sufficient to desensitize the patient to nausea or mouth burn associated with exposure to an increased concentration of capsaicinoid (s) in the next inner layer.

3. The composition of claim 1 in which the increasing concentration of one or more capsaicinoids is a continuous gradient.

4. The composition of claim 1 in which the temporally increasing concentrations of one or more capsaicinoids comprise at least three discrete layers.

5. The composition of claim 4 in the form of a lollipop, in which the inner layer is approximately 2 grams, the middle layer is approximately 4 grams, and the outer layer is approximately 8 grams.

6. The composition of claim 4 in the form of a lollipop, in which the inner layer is approximately 2 grams, the middle layer is approximately 3 grams, and the outer layer is approximately 4 grams.

7. The composition of claim 1, wherein the capsaicinoid is provided in the form of cayenne red pepper.

8. The composition of claim 7 in which the composition is a three layer lollipop and wherein the concentration of cayenne red pepper is approximately 1.0% by weight in the inner layer, approximately 0.5% by weight in the middle layer, and approximately 0.25% by weight in the outer layer.

9. The composition of claim 1 in which the temporally increasing concentrations of one or more capsaicinoids comprise between two and nine discrete layers.

10. The composition of claim 1 wherein the composition is in a form selected from the group consisting of lozenges, lollipops, candies, tablets, caplets, pills, and troches.

11. The composition of claim 1 further comprising an analgesic other than a capsaicinoid.

12. The composition of claim 11 wherein the second analgesic compound is selected from the group consisting of lidocaine and phenol.

13. The composition of claim 1 wherein the capsaicinoid is provided in a form selected from the group consisting of chili pepper, red cayenne pepper, and paprika.

14. The composition of claim 1 wherein the capsaicinoid is selected from the group consisting of capsaicin, norhydrocapsaicin, dihydrocapsaicin, homocapsaicin, homodihydrocapsaicin, nordihydrocapsaicin, homodihydrocapsaicin I, civamide, nonivamide, and NE-19550 (N-[4-hydroxy-3-methoxyphenyl) methyl]-9Z-octadecenamide), NE-21610 (N-[(4-(2-aminoethoxy)-3-methoxyphenyl) methyl]-9Z-octadecenamide, Chemical Abstract Service Registry No. 118 090 17 8), and NE-28345 (N-(9Z-octadecenyl)-3-methoxy-4-hydroxyphenylacetamide, Chemical Abstract Service Registry No. 107 512 56 1).

15. The composition of claim 1 wherein the capsaicinoid has the general formula:

wherein $R_1$ is OH or $OCH_3$, $R_2$ is OH or $OC(O)R_3$, $R_3$ is selected from $C_1$-$C_4$ alkyl, phenyl and methyl, X is NHC(O), NHC(O)O, NHC(O)NH, NHC(S)NH, C(O)NH, or NH(O)S(O), and R is a $C_5$-$C_{23}$ alkyl, $C_5$-$C_{11}$ alkenyl, $C_{11}$-$C_{23}$ cis alkenyl, $C_{11}$-$C_{23}$ alkynyl, $C_{11}$-$C_{23}$ alkadienyl, or $C_{11}$-$C_{23}$ (methylene substituted) alkane.

16. A method for imparting oral or pharyngeal analgesia comprising orally administering to a patient in need thereof a composition in which one or more capsaicinoids is dispersed in a solid or gel vehicle with the concentration of the capsaicinoids decreasing from the center toward the periphery of the vehicle.

17. The method of claim 16 in which the composition contains two or more layers where the outer layer contains a concentration of one or more capsaicinoids which does not cause significant nausea or mouth burn, and is sufficient to desensitize the patient to nausea or mouth burn associated with exposure to the concentration of capsaicinoid(s) in the next inner layer.

18. The method of claim 16 in which the increasing concentration of one or more capsaicinoids is a continuous gradient.

19. The method of claim 16 in which the temporally increasing concentrations of one or more capsaicinoids comprise at least three discrete layers.

20. The method of claim 19 wherein the composition is in the form of a lollipop, in which the inner layer is approximately 2 grams, the middle layer is approximately 4 grams, and the outer layer is approximately 8 grams.

21. The method of claim 19 wherein the composition is in the form of a lollipop, in which the inner layer is approximately 2 grams, the middle layer is approximately 3 grams, and the outer layer is approximately 4 grams.

22. The method of claim 16, wherein the capsaicinoid is provided in the form of cayenne red pepper.

23. The method of claim 22 in which the composition is a three layer lollipop and wherein the concentration of cayenne red pepper is approximately 1.0% by weight in the inner layer, approximately 0.5% by weight in the middle layer, and approximately 0.25% by weight in the outer layer.

24. The method of claim 16 wherein the temporally increasing concentrations of one or more capsaicinoids comprise between two and nine layers.

25. The method of claim 16 wherein the composition is in a form selected from the group consisting of lozenges, lollipops, candies, tablets, caplets, pills, and troches.

26. The method of claim 16 further comprising an analgesic other than a capsaicinoid.

27. The method of claim 26 wherein the second analgesic compound is selected from the group consisting of lidocaine and phenol.

28. The method of claim 16 wherein the capsaicinoid is provided in a form selected from the group consisting of chili pepper, red cayenne pepper, and paprika.

29. The method of claim 16 wherein the capsaicinoid is selected from the group consisting of capsaicin, norhydrocapsaicin, dihydrocapsaicin, homocapsaicin, homodihydrocapsaicin, nordihydrocapsaicin, homodihydrocapsaicin I, civamide, nonivamide, and NE-19550 (N-(3-methoxy-4-hydroxybenzyl) oleamide), NE-21610 (N-[(4-(2-aminoethoxy)-3-methoxyphenyl) methyl]-9Z-octadecenamide) (Chemical Abstract Service Registry No. 118 090 17 8, and NE-28345 (N-(9Z-octadecenyl)-3-methoxy-4-hydroxyphenylacetamide) (Chemical Abstract Service Registry No. 107 512 56 1), and their analogs and derivatives.

30. The method of claim 16 wherein the capsaicinoid has the general formula:

wherein $R_1$ is OH or $OCH_3$, $R_2$ is OH or $OC(O)R_3$, $R_3$ is selected from $C_1$-$C_4$ alkyl, phenyl and methyl, X is NHC(O), NHC(O)O, NHC(O)NH, NHC(S)NH, C(O)NH, or NH(O)S(O), and R is a $C_5$-$C_{23}$ alkyl, $C_5$-$C_{11}$ alkenyl, $C_{11}$-$C_{23}$ cis alkenyl, $C_{11}$-$C_{23}$ alkynyl, $C_{11}$-$C_{23}$ alkadienyl, or $C_{11}$-$C_{23}$ (methylene substituted) alkane.

31. A method of making a composition for the oral delivery of temporally increasing concentrations of one or more capsaicinoids to provide oral or pharyngeal analgesia, wherein the composition comprises one or more capsaicinioids dispersed in a solid or gel vehicle in which the concentration of the capsaicinoid(s) decreases from the center toward the periphery of the vehicle, comprising the steps of forming an inner layer of one or more capsaicinoids dispersed in a solid or gel vehicle, and then forming around the inner layer one or more outer layers each containing successively decreasing concentrations of the capsaicinioid (s).

32. The method of claim 31 in which the composition contains two or more layers, and wherein the outer layer contains a concentration of one or more capsaicinoids which does not cause significant nausea or mouth burn, and is sufficient to desensitize the patient to nausea or mouth burn associated with exposure to the concentration of capsaicinoid(s) in the next inner layer.

33. The method of claim 31 in which the increasing concentration of one or more capsaicinoids is a continuous gradient.

34. The method of claim 31 in which the temporally increasing concentrations of one or more capsaicinoids comprise at least three discrete layers.

35. The method of claim 34 wherein the composition is in the form of a lollipop, in which the inner layer is approximately 2 grams, the middle layer is approximately 4 grams, and the outer layer is approximately 8 grams.

36. The method of claim 34 wherein the composition is in the form of a lollipop, in which the inner layer is approximately 2 grams, the middle layer is approximately 3 grams, and the outer layer is approximately 4 grams.

37. The method of claim 31, wherein the capsaicinoid is provided in the form of cayenne red pepper.

38. The method of claim 31 in which the composition is a three layer lollipop and wherein the concentration of cayenne red pepper is approximately 1.0% by weight in the inner layer, approximately 0.5% by weight in the middle layer, and approximately 0.25% by weight in the outer layer.

39. The method of claim 31 wherein the temporally increasing concentrations of one or more capsaicinoids comprise between two and nine layers.

40. The method of claim 31 wherein the composition is in a form selected from the group consisting of lozenges, lollipops, candies, tablets, caplets, pills, and troches.

41. The method of claim 31, further comprising the step of adding to one or more layers an analgesic other than a capsaicinoid.

42. The method of claim 41, wherein the second analgesic compound is selected from the group consisting of lidocaine and phenol.

43. The method of claim 31 wherein the capsaicinoid is provided in a form selected from the group consisting of chili pepper, red cayenne pepper, and paprika.

44. The method of claim 31 wherein the capsaicinoid is selected from the group consisting of capsaicin, norhydrocapsaicin, dihydrocapsaicin, homocapsaicin, homodihydrocapsaicin, nordihydrocapsaicin, homodihydrocapsaicin I, civamide, nonivamide, and NE-19550 (N-(3-methoxy-4-hydroxybenzyl) oleamide), NE-21610 (N-[(4-(2-aminoethoxy)-3-methoxyphenyl) methyl]-9Z-octadecenamide) (Chemical Abstract Service Registry No. 118 090 17 8, and NE-28345 (N-(9Z-octadecenyl)-3-methoxy-4-hydroxyphenylacetamide) (Chemical Abstract Service Registry No. 107 512 56 1), and their analogs and derivatives.

45. The method of claim 31 wherein the capsaicinoid has the general formula:

wherein $R_1$ is OH or $OCH_3$, $R_2$ is OH or $OC(O)R_3$, $R_3$ is selected from $C_1$–$C_4$ alkyl, phenyl and methyl, X is NHC(O), NHC(O)O, NHC(O)NH, NHC(S)NH, C(O)NH, or NH(O)S(O), and R is a $C_5$–$C_{23}$ alkyl, $C_5$–$C_{23}$ alkenyl, $C_{11}$–$C_{23}$ cis alkenyl, $C_{11}$–$C_{23}$ alkynyl, $C_{11}$–$C_{23}$ alkadienyl, or $C_{11}$–$C_{23}$ (methylene substituted) alkane.

* * * * *